United States Patent
Myers (10) Patent No.: US 10,534,107 B2
(45) Date of Patent: Jan. 14, 2020

(54) GROSS MINERALOGY AND PETROLOGY USING RAMAN SPECTROSCOPY

(71) Applicant: GAS SENSING TECHNOLOGY CORP., Laramie, WY (US)

(72) Inventor: Grant A. Myers, Laramie, WY (US)

(73) Assignee: GAS SENSING TECHNOLOGY CORP., Laramie, WI (US)

( * ) Notice: Subject to any disclaimer, the term of this patent is extended or adjusted under 35 U.S.C. 154(b) by 0 days.

(21) Appl. No.: 15/594,361

(22) Filed: May 12, 2017

(65) Prior Publication Data

US 2017/0329045 A1 Nov. 16, 2017

Related U.S. Application Data (60) Provisional application No. 62/336,035, filed on May 13, 2016.

(51) Int. Cl.

| | |
|---|---|
| *G01B 11/30* | (2006.01) |
| *G01V 8/00* | (2006.01) |
| *G01V 8/10* | (2006.01) |
| *E21B 49/02* | (2006.01) |
| *G01N 21/65* | (2006.01) |
| *G01N 33/24* | (2006.01) |
| *G02B 21/36* | (2006.01) |

(Continued)

(52) U.S. Cl.
CPC ............ *G01V 8/10* (2013.01); *E21B 49/02* (2013.01); *G01B 11/303* (2013.01); *G01N 21/65* (2013.01); *G01N 33/24* (2013.01); *G02B 21/365* (2013.01); *G06T 7/0004* (2013.01); *G06T 7/40* (2013.01); *G02B 21/06* (2013.01); *G06T 2207/30181* (2013.01)

(58) Field of Classification Search
CPC ........ G01V 8/10; G01N 21/65; G01N 21/718; G01N 21/31; G01N 21/3563; G01N 21/6408; G01N 21/21; G01N 33/24; G06T 7/40; G06T 2207/30181; G06T 7/0004; G02B 23/24; G02B 21/06; G02B 21/365; G01B 11/303; E21B 49/02

See application file for complete search history.

(56) References Cited

U.S. PATENT DOCUMENTS 5,315,113 A * 5/1994 Larson ................. G01N 23/227
 250/305
5,644,550 A * 7/1997 Priest ....................... G01V 1/50
 367/35

(Continued)

FOREIGN PATENT DOCUMENTS

WO 2014022757 A1 2/2014

OTHER PUBLICATIONS

Liang Gao, "Snapshot Image Mapping Spectrometer (IMS) with high sampling density for hyperspectral microscopy"—SPIE Jul. 5, 2010 / vol. 18, No. 14 / Optics Express (Year: 2010).*

(Continued)

*Primary Examiner* — Philip P. Dang
(74) *Attorney, Agent, or Firm* — Adolph Locklar (57) ABSTRACT

A method may include measuring a formation sample using a Raman spectrometer to determine a formation sample characteristic, wherein the formation sample characteristic is mineral ID and distribution, carbon ID and distribution, thermal maturity, rock texture, fossil characterization, or combinations thereof.

9 Claims, 9 Drawing Sheets

(51) Int. Cl.
*G06T 7/00* (2017.01)
*G06T 7/40* (2017.01)
*G02B 21/06* (2006.01)

(56) References Cited

U.S. PATENT DOCUMENTS

| | | | | |
|---|---|---|---|---|
| 6,375,817 | B1* | 4/2002 | Taylor | B01L 3/502784 204/453 |
| 7,061,605 | B2* | 6/2006 | Lemmo | B01J 19/0046 356/300 |
| 7,381,529 | B2* | 6/2008 | Yamakawa | C12Q 1/6874 435/6.1 |
| 7,405,395 | B2* | 7/2008 | Ellson | G01N 33/54393 250/288 |
| 7,511,813 | B2* | 3/2009 | Vannuffelen | G01J 3/18 250/269.1 |
| 7,564,546 | B2* | 7/2009 | Maier | G01J 3/2803 356/301 |
| 8,189,877 | B2* | 5/2012 | Asner | G06T 7/00 348/144 |
| 8,363,225 | B2* | 1/2013 | Rolland | G01B 9/021 356/479 |
| 8,484,759 | B2* | 7/2013 | Jesse | G01Q 60/58 374/100 |
| 8,489,356 | B2* | 7/2013 | Proksch | G01Q 10/06 250/492.22 |
| 8,595,859 | B1* | 11/2013 | Rankl | B82Y 35/00 73/105 |
| 9,366,693 | B2* | 6/2016 | Proksch | G01Q 210/00 |
| 9,414,780 | B2* | 8/2016 | Rhoads | G06F 16/245 |
| 9,494,522 | B2* | 11/2016 | Berto | G01N 21/65 |
| 9,562,849 | B2* | 2/2017 | Kester | G01J 3/2823 |
| 9,756,263 | B2* | 9/2017 | Kester | G06K 9/22 |
| 9,851,304 | B2* | 12/2017 | Fuhr | G01N 21/65 |
| 9,970,888 | B2* | 5/2018 | Szudajski | G01N 21/65 |
| 10,119,901 | B2* | 11/2018 | Casas | H04N 1/2191 |
| 10,139,279 | B2* | 11/2018 | Pluvinage | G01J 3/2823 |
| 2006/0211071 | A1* | 9/2006 | Andre | C12Q 1/56 435/13 |
| 2007/0244395 | A1* | 10/2007 | Wang | A61B 5/0059 600/476 |
| 2013/0056626 | A1 | 3/2013 | Shen et al. | |
| 2014/0378810 | A1* | 12/2014 | Davis | G06F 16/245 600/407 |
| 2015/0247190 | A1* | 9/2015 | Ismagilov | C12Q 1/6851 506/9 |
| 2015/0323516 | A1 | 11/2015 | Washburn | |
| 2016/0340570 | A1 | 11/2016 | Salla et al. | |
| 2018/0020913 | A1* | 1/2018 | Grundfest | G02B 5/10 351/206 |

OTHER PUBLICATIONS

International Search Report and Written Opinion issued in PCT App. No. PCT/US2017/032529, dated Sep. 25, 2017 (10 pages).

* cited by examiner

GROSS MINERALOGY AND PETROLOGY USING RAMAN SPECTROSCOPY

CROSS-REFERENCE TO RELATED APPLICATIONS

This application is a nonprovisional application which claims priority from U.S. provisional application No. 62/336,035, filed May 13, 2016, which is hereby incorporated by reference in its entirety.

TECHNICAL FIELD/FIELD OF THE DISCLOSURE

The present disclosure relates generally to methods and apparatuses for evaluating gross mineralogy and petrology of a geologic formation.

BACKGROUND OF THE DISCLOSURE

The depositional processes that created certain geologic formations (hereinafter, "formations"), for example, hydrocarbon-bearing formations, and diagenetic processes that reformed portions of the hydrocarbon-bearing formations were heterogeneous. Knowledge of the gross mineralogy and petrology of a formation and/or sections of a formation may provide insight into areas of interest in the formation. For instance, gross mineralogy and petrology may identify spots for fracking, for instance, in a shale formation.

Traditional methods of determination of gross mineralogy and petrography are performed on formation samples with different sets of equipment and require some degree of qualitative analysis by a geologist. These traditional methods often are subjective and may result in misidentification of gross mineralogy and petrography characteristics. For instance, X-Ray Diffraction (XRD) may provide gross mineralogy of a homogenized sample, but such characteristics as grain size, pore size, and crystalline structure are lost in the sample preparation. XRD also does not provide a measure of organics of the formation sample. SEM/EDS (Scanning Electron Microscope/Energy Dispersive X-ray Spectroscopy) may identify grain size and structure of a formation sample, but does not provide a direct molecular analysis. In addition, EDS is limited to elemental analysis and neither EDS nor SEM provides a measure of organics of the formation sample. X-Ray Fluorescence (XRF) is limited to elemental analysis, which may require correlation to equate the elemental analysis to mineralogy of a sample. XRF does not provide a measure of organics of the formation sample. Laser-induced breakdown spectroscopy (LIBS), like XRF, is limited to elemental analysis and does not provide a measure of organics in the formation sample. LIBS vaporizes a portion of the formation sample, which may affect reproducibility of the results. Pyrolysis may determine thermal maturity of a formation sample, but the formation sample is physically and chemically altered in this destructive test, adversely impacting reproducibility of results. Further, pyrolysis results may be skewed by the presence of bitumen in a formation sample.

SUMMARY

The present disclosure provides for a method. The method includes measuring a formation sample using a Raman spectrometer to determine a formation sample characteristic, wherein the formation sample characteristic is mineral ID and distribution, carbon ID and distribution, thermal maturity, rock texture, fossil characterization, or combinations thereof.

The present disclosure further provides for a method. The method includes imaging a sample surface, generating a digital atlas substrate, mapping an area of interest, and layering information on a digital atlas substrate.

BRIEF DESCRIPTION OF THE DRAWINGS

The present disclosure may be understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

A detailed description will now be provided. The following disclosure includes specific embodiments, versions and examples, but the disclosure is not limited to these embodiments, versions or examples, which are included to enable a person having ordinary skill in the art to make and use the disclosure when the information in this application is combined with available information and technology.

Various terms as used herein are shown below. To the extent a term used in a claim is not defined below, it should be given the broadest definition persons in the pertinent art have given that term as reflected in printed publications and issued patents. Further, unless otherwise specified, all compounds described herein may be substituted or unsubstituted and the listing of compounds includes derivatives thereof.

Further, various ranges and/or numerical limitations may be expressly stated below. It should be recognized that unless stated otherwise, it is intended that endpoints are to be interchangeable. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.).

"Formation" as used herein is a body of strata of predominantly one type or combination of types. A formation may include one or more "intervals," which are subdivisions of a formation. A "hydrocarbon-bearing formation" is a formation in which one or more intervals include at least one hydrocarbon.

In certain embodiments of the present disclosure, a formation sample measurement instrument, such as a Raman spectrometer, or a Raman spectrometer in conjunction with other technologies including, but not limited to XRD, SEM/EDS, infrared (IR) microscopy, XRF, LIBS, and digital optical microscopy (hereinafter referred to as "non-Raman technology") may be used to measure formation sample characteristics. In some embodiments, a particular formation sample characteristic may be measured with a Raman spectrometer. In other embodiments, a particular formation sample characteristic may be measured with a non-Raman technology. In certain embodiments, a formation sample characteristic may be measured with a Raman spectrometer and the same characteristic may be measured with a non-Raman spectrometer. In other embodiments, a formation sample characteristic may be measured with a non-Raman technology and the same characteristic may be measured with a Raman spectrometer or a different non-Raman technology. In some embodiments, the Raman spectrometer uses confocal Raman spectroscopy to measure the characteristics of the formation sample.

Examples of characteristics of a formation sample may include, but are not limited to, optical image, mineral identification ("ID") and distribution, carbon and/or organic matter ID and distribution, thermal maturity, rock texture, lithology and fossil characterization. An optical image is an image of the formation sample or a portion of the formation sample formed by the refraction or reflection of light. Mineral ID and distribution is the identification of minerals in the formation sample and their location within the formation sample. Mineral ID and distribution includes, but is not limited to clay identification and distribution. Carbon and/or organic matter ID and distribution is the differentiation of different carbon types and or organic phases within the formation sample, such as kerogen and bitumen, and the distribution of those carbon types and organic phases within the formation sample. Thermal maturity is the extent of heat-driven reactions that alter the composition of organic matter, including, but not limited to, the conversion of sedimentary organic matter to petroleum or cracking of oil to gas. Rock texture of a formation sample includes grain size distribution, pore size distribution, mineral phase distribution, grain orientation, grain shape and angularity, porosity distribution, and bedding planes. Fossil characterization includes the identification, distribution and measurement of fossil markers and associated organic and inorganic material with Raman or other non-Raman technology.

Figure 6:
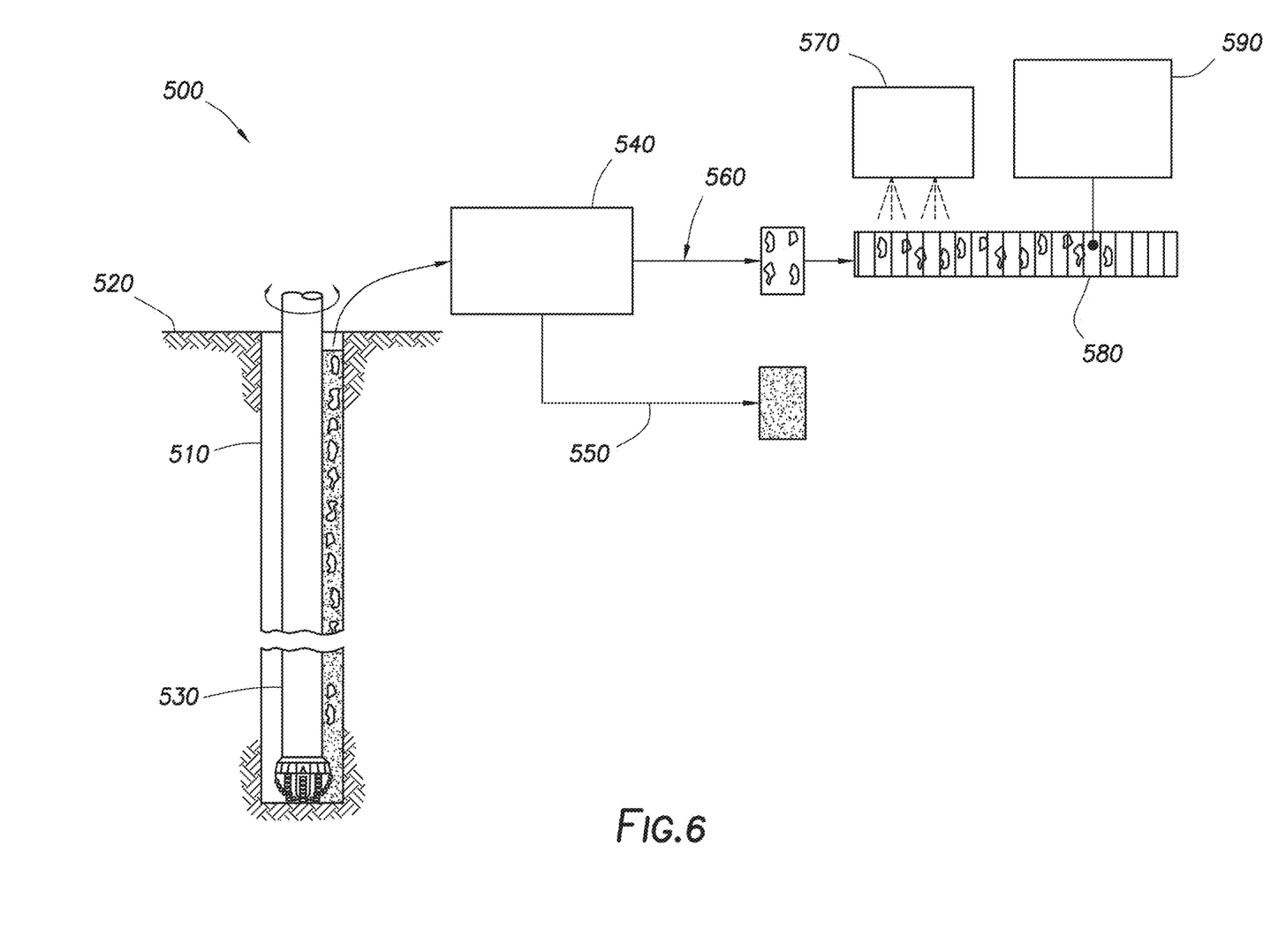
FIG. 6 is an ex-situ measurement system consistent with certain embodiments of the present disclosure.

Measurement of formation samples may be performed ex-situ or in-situ. In ex-situ measurement, a formation sample is removed from the formation. For example and without limitation, removal of a formation sample may be through retrieval of a core sample from the formation, by capture of drill cuttings, such as from a shale shaker, chemical extraction or obtaining a homogenized powder . . . . In certain embodiments, the formation sample may be transported to a measurement facility (either on the wellsite or elsewhere), such as a laboratory, or removed from process equipment such as a shale shaker. Measurements are performed through the use of the formation sample measurement instrument, such as a Raman spectrometer or by non-Raman technology. An example of measurement system for measurement of formation samples ex-situ is depicted in FIG. 6. FIG. 6 depicts ex-situ measurement system 500. In ex-situ measurement system 500, drill string 530 is positioned within wellbore 510. As drilling is performed by drill string 530, wellbore fluid containing cuttings, drilling mud, and formation fluids, for example, are withdrawn from wellbore 510 to surface 520. The wellbore fluid is separated by cuttings separator 540. Cuttings separator 540 may be, for example and without limitation, a shale shaker. Drilling mud is removed from cuttings separator 540 through drilling mud discharge 550 and cuttings are removed from cuttings separator 540 through cuttings discharge 560. Cuttings may be cleaned and otherwise processed in cleaning system 570 to ready the cuttings for analysis. The cleaned cuttings may then be analyzed using analyzer 590. Analyzer 590 may be a Raman spectrometer or a non-Raman spectrometer. In some embodiments, cuttings may be transported using sample conveyance 580 through cleaning system 570 and to analyzer 590 using sample conveyance 580. Sample conveyance 580 may be a conveyor, carousel, or other moving system. In other embodiments, analyzer 590 may be positioned in a probe that translates over sample cuttings.

In in-situ measurement, the formation sample measurement instrument as described hereinbelow is positioned in the formation, such as into a wellbore, and measurements performed on the formation itself, for instance, the wall of the wellbore. While measurement of formation sample characteristics are described below with respect to ex-situ measurement, one of ordinary skill in the art with the benefit of this disclosure will understand that the measurements may be made in-situ as well.

The formation sample measurements may be collected in a digital atlas. In a digital atlas, formation characteristics of portions of the formation sample may be associated or "layered," allowing a user to analyze, query, overlay, create animations, perform a digital zoom, or scroll and pan over the digital representation of the formation sample.

High-Resolution Digital Optical Microscopy

Figure 1:
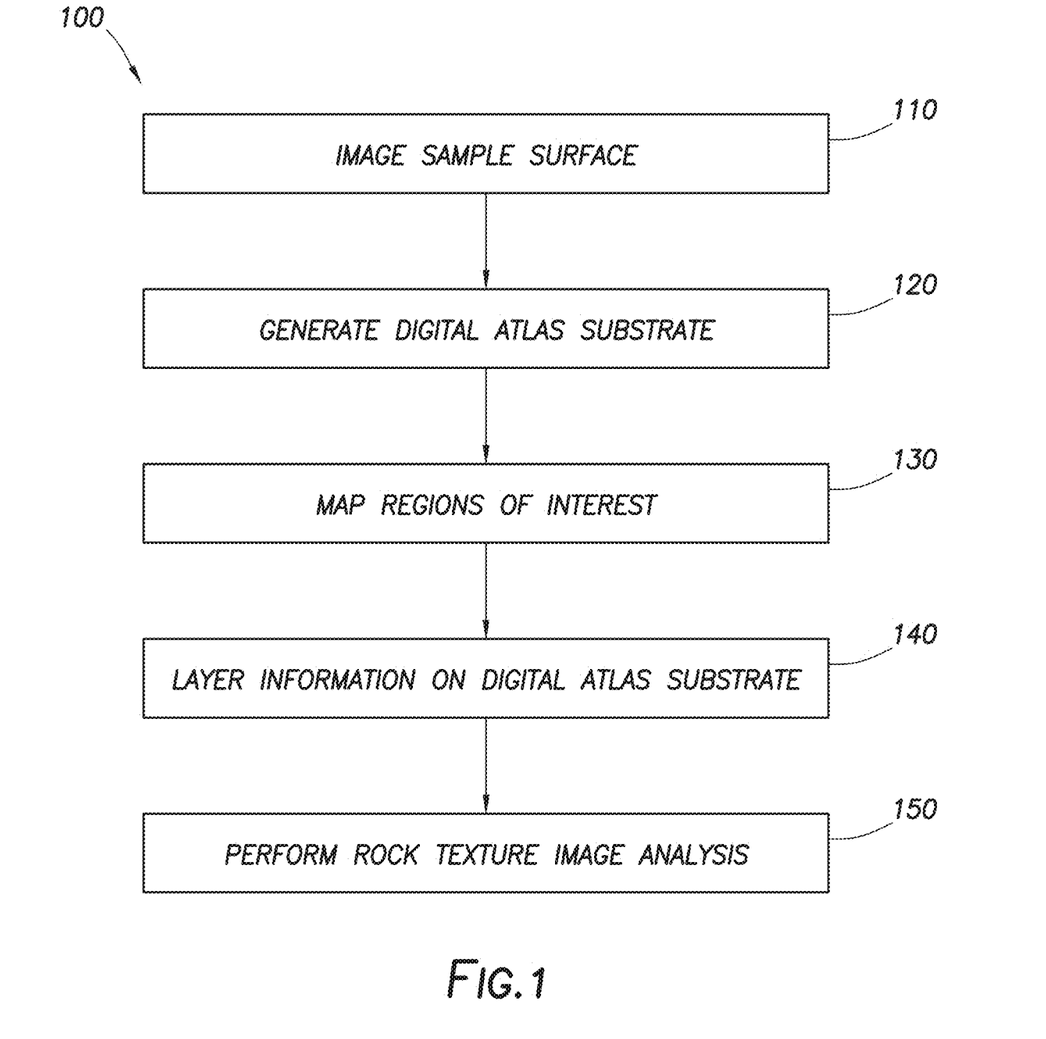
FIG. 1 is a flowchart depicting the formation of a digital atlas consistent with at least one embodiment of the present disclosure.

In certain embodiments, as shown in FIG. 1, digital atlas formation 100 may begin by imaging the formation sample surface (image sample surface 110) using, for example, automated high-resolution digital optical microscopy. In image sample surface 110, formation samples may be fixed to a mounting substrate and placed on an encoded XYZ-microscope stage for optical imaging using, for instance, wide-field illumination techniques. Wide-field illumination techniques include, but are not limited to, conventional reflective or transmissive illumination, polarized light, fluorescence, and dark-field. Images of formation sample surfaces may be captured on a digital camera through a microscope objective and digitally stored in a non-transitory media. In certain embodiments, the formation sample may be moved through the field of view of the microscope objective, or the field of view may be moved over the sample using a digital sample methodology. In certain embodiments, such as in-situ measurement, the formation sample measurement instrument may be moved over the formation. In yet other embodiments, laser scanning may be performed where a focused laser spot is optically translated across a fixed sample surface.

Figure 2A:
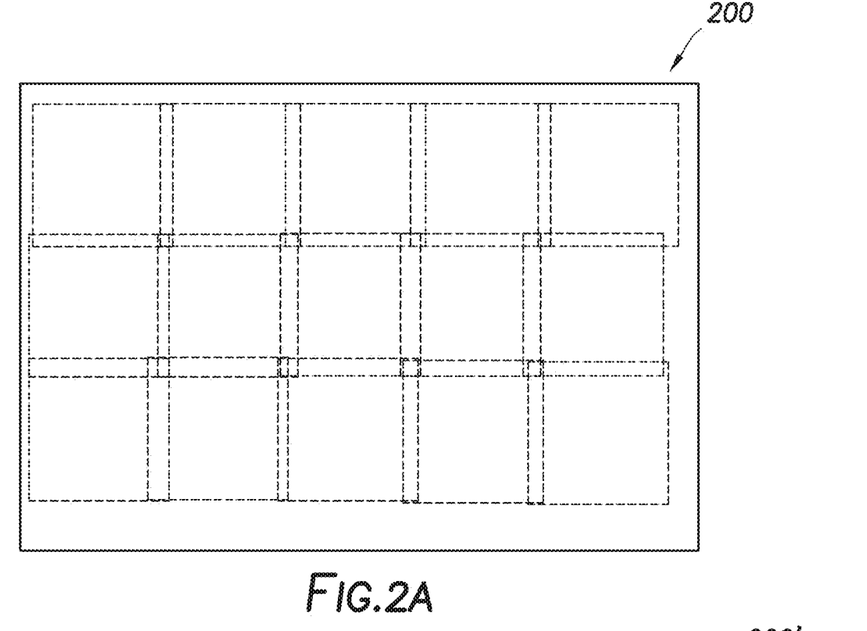
FIGS. 2A, 2B are graphical depictions of digital sampling methodology consistent with embodiments of the present disclosure.
Figure 2B:
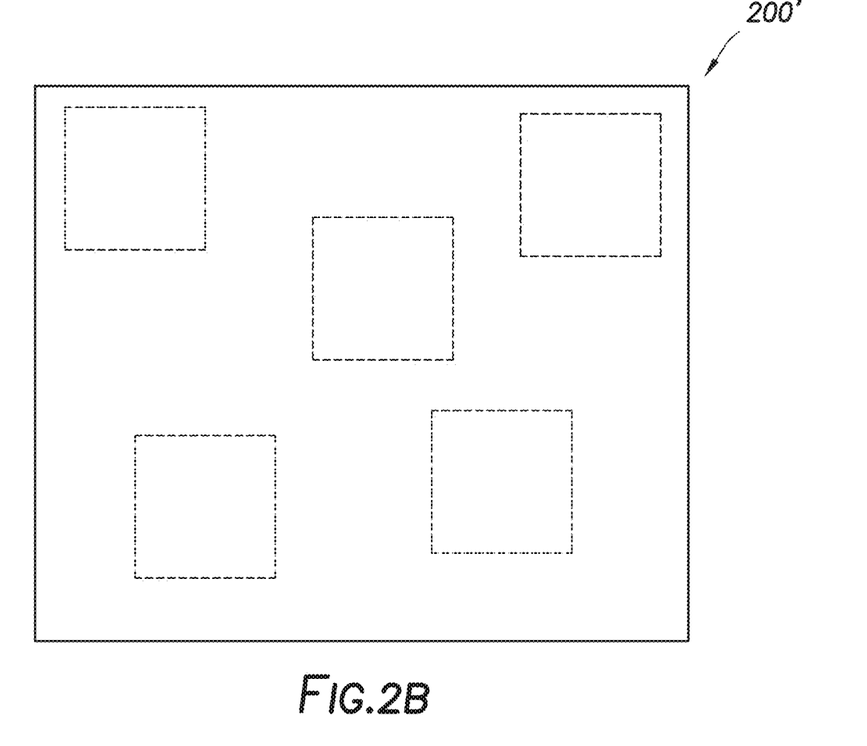

With direction to FIG. 2A, digital sample methodology 200 may include overlapping images of the formation sample surface. As shown in FIG. 2B, digital sample methodology 200' may include representative, selected, or randomly determined images of the sample surface. Representative images may be images determined optically by a user or via algorithm to be representative of the formation sample surface. Selected images may be images of a formation sample surface determined optically to be of interest, such as, for example, examination by a user using the naked eye.

"Of interest" portions of sample surface may be microfractures, fossils, coloration changes, organic features, inorganic features, specific formation beds or other portions of the sample. Random images may be selected by random computer algorithm, for example. The images captured by the encoded microscope stage may be used to generate a digital atlas substrate of formation sample surfaces (element 120 of FIG. 1). In addition to capturing images to form the digital atlas substrate, images captured by the encoded microscope stage may be used to develop 3-D topography of the formation sample surface. The 3-D topography may be developed by identifying regions in the image which are in focus. Additionally, images captured by the encoded microscope stage may be used to identify areas of interest for further study by hyperspectral mapping microscopy as described herein below, and analyze rock texture as described herein below. Information regarding 3-D topography of the formation sample surface and rock texture may be "layered" onto the digital atlas substrate to form the digital atlas in layer information on digital atlas substrate 140 in FIG. 1. "Layering," as described herein, means associating information regarding the formation sample surface with the particular image or portion of a particular image to which it pertains. In certain embodiments, information regarding the formation sample surface may be associated with, i.e., layered onto, individual pixels or groups of pixels of the images. Optical microscopy may be performed at optical resolution. Optical resolution may refer to a scale of greater than 500 nm.

In certain embodiments, in addition to, or in lieu of, optical microscopy, the digital atlas substrate may be formed through use of images obtained from SEM. In other embodiments, images obtained from SEM may be used as a layer in the digital atlas substrate.

Hyperspectral Mapping Microscopy

In certain embodiments, areas of interest may be identified from the high-resolution digital microscopy and may be examined using hyperspectral mapping microscopy (130). In certain embodiments, image sample surface (110) may be omitted and hyperspectral mapping microscopy may be performed on portions of the sample surface otherwise identified as of interest, such as, for example, by visual identification. Hyperspectral mapping microscopy may be performed, for instance, using sample-scanning spectroscopy or XRF. Examples of sample-scanning spectroscopy include LIBS, IR, fluorescence, time-resolved spectroscopy, and confocal laser microscopy, such as, for example and without limitation, Raman spectroscopy. Sample-scanning confocal laser microscopy may be performed by focusing an excitation laser through the microscope objective to form a diffraction-limited focused laser spot onto sample surfaces in areas of interest identified through automated high-resolution digital microscopy. By focusing the diffraction-limited focused laser spot on the formation sample, light is emitted from the formation sample. Light emitted from the formation sample in the diffraction-limited focused laser spot may be collected and passed through a spectrograph, such as a Raman spectrograph, for separation by wavelength and analysis of the emitted light spectrum through use of, for instance, a digital camera. The encoded XYZ-microscope stage may be used to raster the sample surface through the laser focus and record emitted light spectra from focused spots to generate a hyperspectral multi-point scan, line scan or map of the emitted light in the area of interest.

Individual light spectra may be compared to a library of, for example, Raman spectra of minerals, clays, and organic phases to identify rock constituents, the abundance of rock constituents and distribution of rock constituents. One example of a digital library is the RRUFF project. Examples of rock constituents may include, for example, mineral types, quartz, clay-types (including, but not limited to swelling clays and non-swelling clays), kerogen types, and bitumen. By identifying the rock constituents, the abundance of rock constituents and the distribution of rock constituents, formation characteristics such as quartz-to-clay ratio (a measure of rock brittleness), clay type, and total organic content (TOC) may be calculated. In certain embodiments, spectral analysis, such as of organic phases, may include peak-fitting, factor analysis and other chemometrics techniques to correlate the complex Raman spectra of organic deposits with carbon types (e.g. kerogen and bitumen) and thermal maturity indices.

For purposes of this disclosure, chemometrics is the application of data analysis techniques to analyze usually large amounts of chemical data. In certain embodiments, chemometrics analysis may be used to identify relationships between observable and underlying (latent) variables and to predict behaviors or properties of systems, for example in a calibration. Applied to spectroscopic chemical data, including, but not limited to Raman spectra, chemometrics analyses may be based on the principal of superposition, i.e., a spectrum is composed of the sum of its parts. For example and without limitation, the Raman spectrum from a mixture of non-interacting chemicals can be reconstituted by summing the individual Raman spectra from each of the components in the mixture. Examples of chemometrics techniques for spectral data include Principal Components Analysis, which seeks to reduce the data to a minimum number of components, Factor Analysis, which seeks to understand relationships between variables in data, Classical Least Squares analysis, which is based on linear combinations of measured pure components and Partial Least Squares analysis, an inverse least squares technique that seeks to correlate the variance in the independent and dependent variables of the data set, working in absence of measured pure components.

Information obtained from hyperspectral mapping microscopy, including but not limited to rock constituents, the abundance of rock constituents and distribution of rock constituents, quartz-to-clay ratios, clay type, and total organic content (TOC) may be layered on to the digital atlas substrate (140).

In other embodiments, a laser wavelength is selected to excite the fluorescence of rock constituents and a hyperspectral fluorescence map is recorded to identify and analyze the intensity and distribution of fluorescent constituents, such as Tasmanites fossils. In another alternative, the excitation is tuned to the infrared and an absorbance spectrum map is collected. In yet another alternative, pulsed laser is focused on the sample and a time-gated detector is implemented to collect time-resolved spectral maps (e.g. fluorescence lifetime) or elemental maps are performed through laser-induced breakdown spectroscopy (LIBS). This information may be layered onto the digital atlas substrate (140).

Rock Texture Image Analysis:

In certain embodiments, rock texture image analysis (element 150 in FIG. 1) may be performed on the digital atlas for a formation sample. Optical imaging and hyperspectral mapping may generate a large amount of rock formation image data that contains information about the makeup and texture of the rock of the formation sample, i.e., the rock fabric. Advanced image analysis techniques may be used on the rock formation image data to characterize, for instance, the size of grains and pore spaces of the formation sample or portion of the formation sample.

The compilation of images and data in the digital atlas may be processed using one or more image processing techniques. Some information, such as a digital atlas layer corresponding to the distribution of pyrite as identified with for example, hyperspectral Raman mapping or SEM/EDS elemental analysis, may be analyzed for mineral grain size, grain shape, and distribution. Example image processing techniques include, but are not limited to, color-based segmentation, shape identification, Hough Transforms, color inversion, boundary tracing, Red/Green/Blue (RGB) color map filtering, distribution statistics, noise removal and image morphology or morphological operations such as dilation and contraction. To perform these techniques, images may be enhanced to increase contrast, or color saturation. Some steps may be performed manually. Shapes such as circles, rectangles, squares, and triangles may be fit to particular features, either visual features, or specific features identified by spectral analysis, such as pyrite or quartz.

By applying digital image processing, the need for a highly trained person may be removed, and the analysis performed objectively. The algorithms and processing can be done on the entire image, or on specific areas of interest identified through steps such as high resolution imaging, or hyperspectral mapping.

Figure 7:
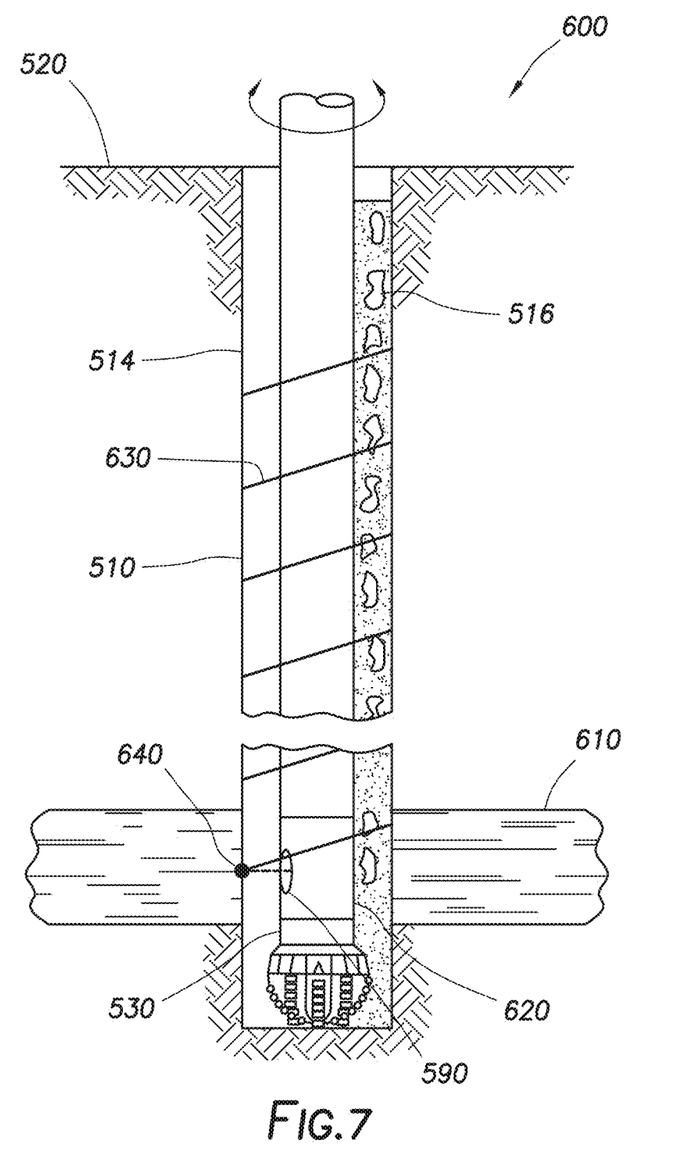
FIG. 7 is an in-situ measurement system consistent with certain embodiments of the present disclosure.

In certain embodiments, determination of formation characteristics may be performed in-situ. For instance, during drilling, a Raman spectrometer, or a Raman spectrometer in conjunction with non-Raman technology, hereinafter referred to as the "in-situ measurement tool" may be included as part of an MWD/LWD string, tubular deployed method, or fiber optic string. The in-situ measurement tool may rotate with the drill string, moving the field of view, for instance, in a helical path, and the sidewall of a borehole may be examined. In other embodiments, the in-situ measurement tool may measure the formation characteristics by measuring drill cuttings that flow past the in-situ measurement tool. In embodiments where the sidewall or cuttings are measured, results may be bulk averaged for mineral analysis, identification of organics, lithologies and formations, and total organic carbon. An example of an in-situ measurement system is depicted in FIG. 7. In-situ measurement system 600 may include in-situ measurement tool 620 which includes analyzer 590. Analyzer 590 may be a Raman spectrometer, or a Raman spectrometer in conjunction with non-Raman technology. In-situ measurement tool 620 is positioned within wellbore 510. As further shown in FIG. 7, in-situ-measurement tool 620 may use helical path 630 to reach formation of interest 610. Analyzer spot 640 may be projected against wellbore wall 514 and/or drill cuttings 516 (shown as analyzer spot 640, which may be a laser spot) along helical path 630, thereby moving the field of view of analyzer 590.

Figure 8:
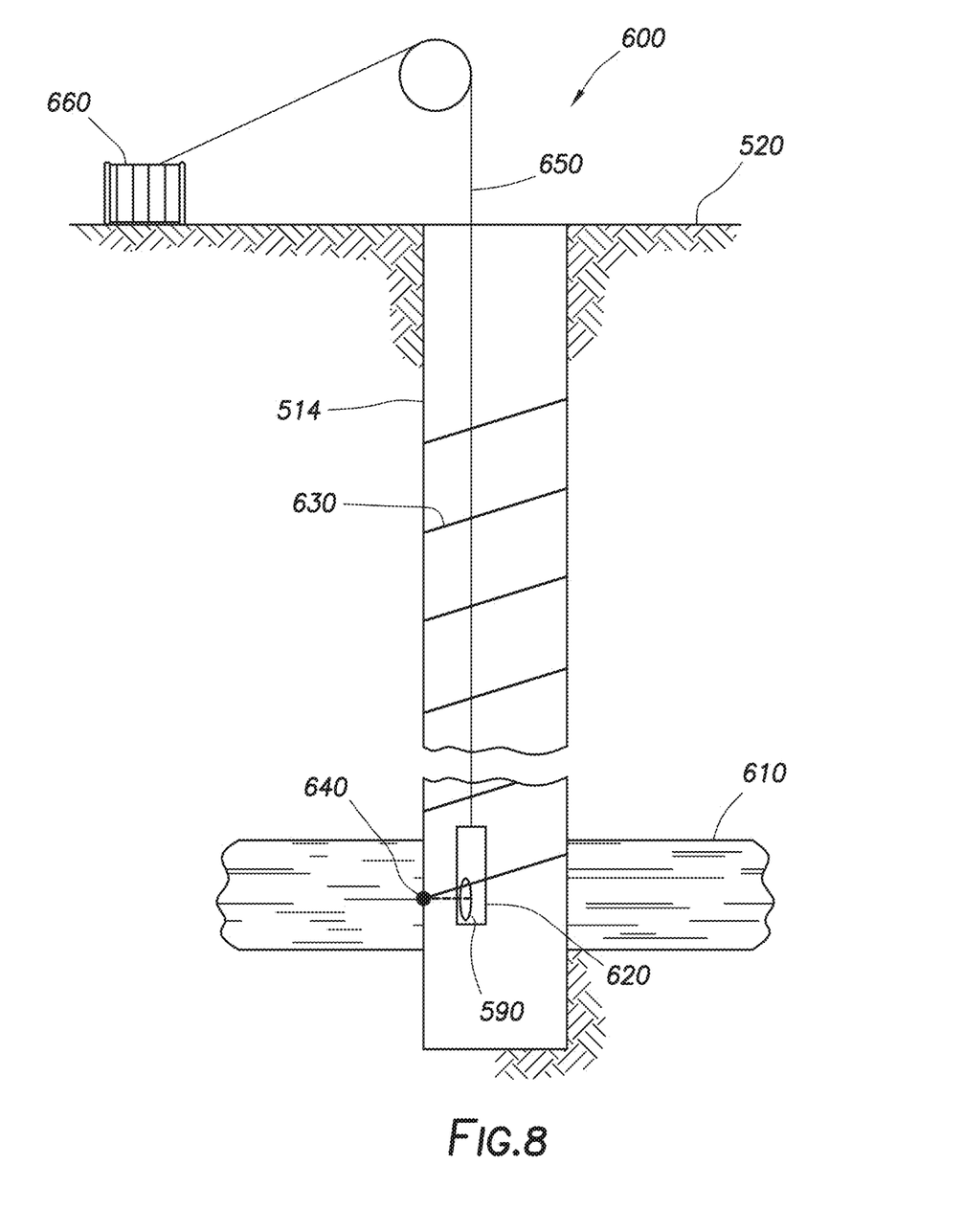
FIG. 8 is an in-situ measurement system consistent with certain embodiments of the present disclosure.
Figure 9:
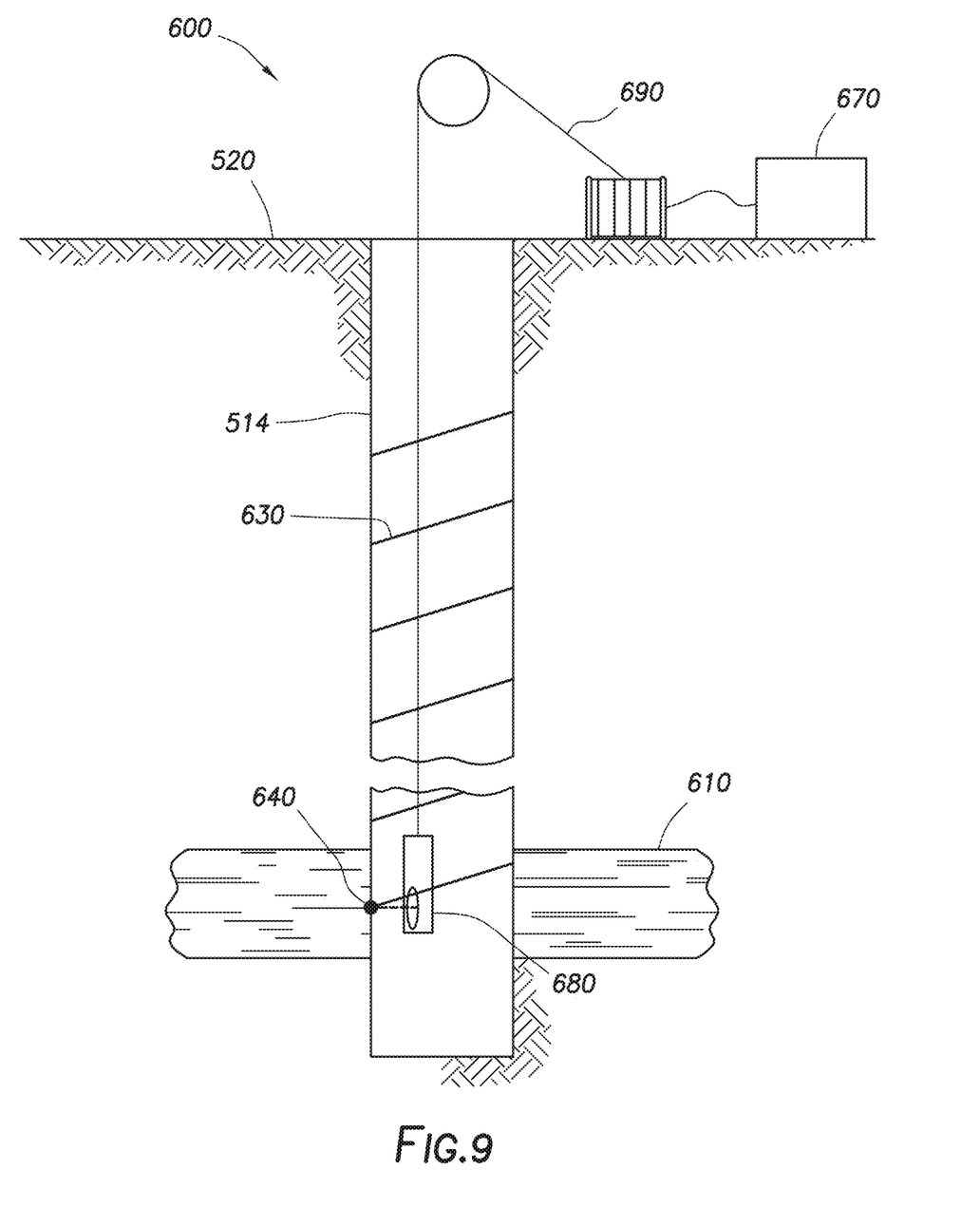
FIG. 9 is an in-situ measurement system consistent with certain embodiments of the present disclosure.

In other embodiments, after completion of drilling, an in-situ measurement tool may be lowered into the formation via wireline. By rotating the in-situ measurement tool, for instance, in a helical path, the sidewall of a borehole may be examined. The in-situ measurement tool could use a laser scanning and optical technique to translate the laser across the sidewall surface. In another embodiment, the in-situ measurement tool could be conveyed into the formation via coiled tubing or similar tubular type deployment. An example of such an in-situ measurement system is shown in FIG. 8. FIG. 8 depicts uses of in-situ measurement system 600 after completion of drilling. In-situ measurement tool 620 may be lowered along helical path 630. Analyzer spot 640 may be projected against wellbore wall 514 along helical path 630, thereby moving the field of view of analyzer 590. In-situ measurement tool 620 may be lowered into wellbore 510 using wirelines or tubing conveyance 660, which connects with wireline or tubing 650 to in-situ measurement tool 620. Additionally, an in-situ measurement tool could use a caliper or other similar device to move the tool against the side of the wellbore and interrogate a specific area. Additionally, in yet another option, the in-situ measurement tool could be a fiber optic conveyed system where, for example, a probe is located at the end of the fiber optic and part or all of the remaining components of the Raman spectrometer or non-Raman technology is at the surface. An example of such an embodiment is depicted in FIG. 9. FIG. 9 includes in-situ measurement system 600. Probe 680 is conveyed via fiber optic cable 690 into wellbore 510 to formation of interest 610 along helical path 630. Spectrometer 670 and associated electronics may be located on surface 520.

EXAMPLES

The disclosure having been generally described, the following examples show particular embodiments of the disclosure. It is understood that the example is given by way of illustration and is not intended to limit the specification or the claims.

Example 1

Hyperspectral Raman maps may reveal the location of chemical domains. Image segmentation analysis of domains may characterize the count, distribution, size, shape, and structure of domains. In a thin section, mounting material, e.g. epoxy, may infiltrate large pores and fractures. Mounting material may have a characteristic Raman or fluorescence signature, or a unique color, and so may be identified and characterized as to size, shape, and distribution in hyperspectral maps or digital atlas images. In Example 1, mounting material domains are to be identified by applying a filter to the image to show the RGB pixels that match the color of the mounting material. A statistical distribution of these pixel locations, and size of colored regions may be used to indicate the porosity and pore sizes.

Example 2

Figure 3:
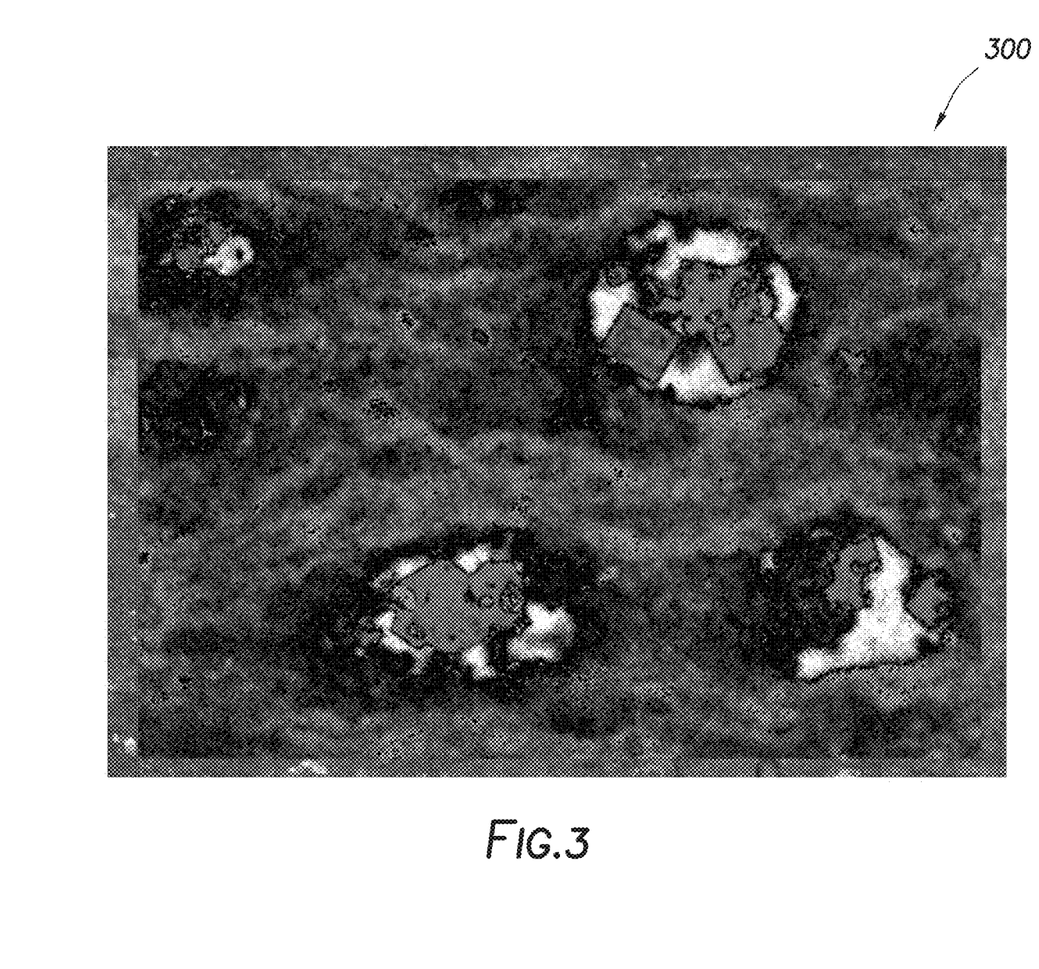
FIG. 3 is a combined optical and false color hyperspectral image as described in Example 2.
Figure 4:
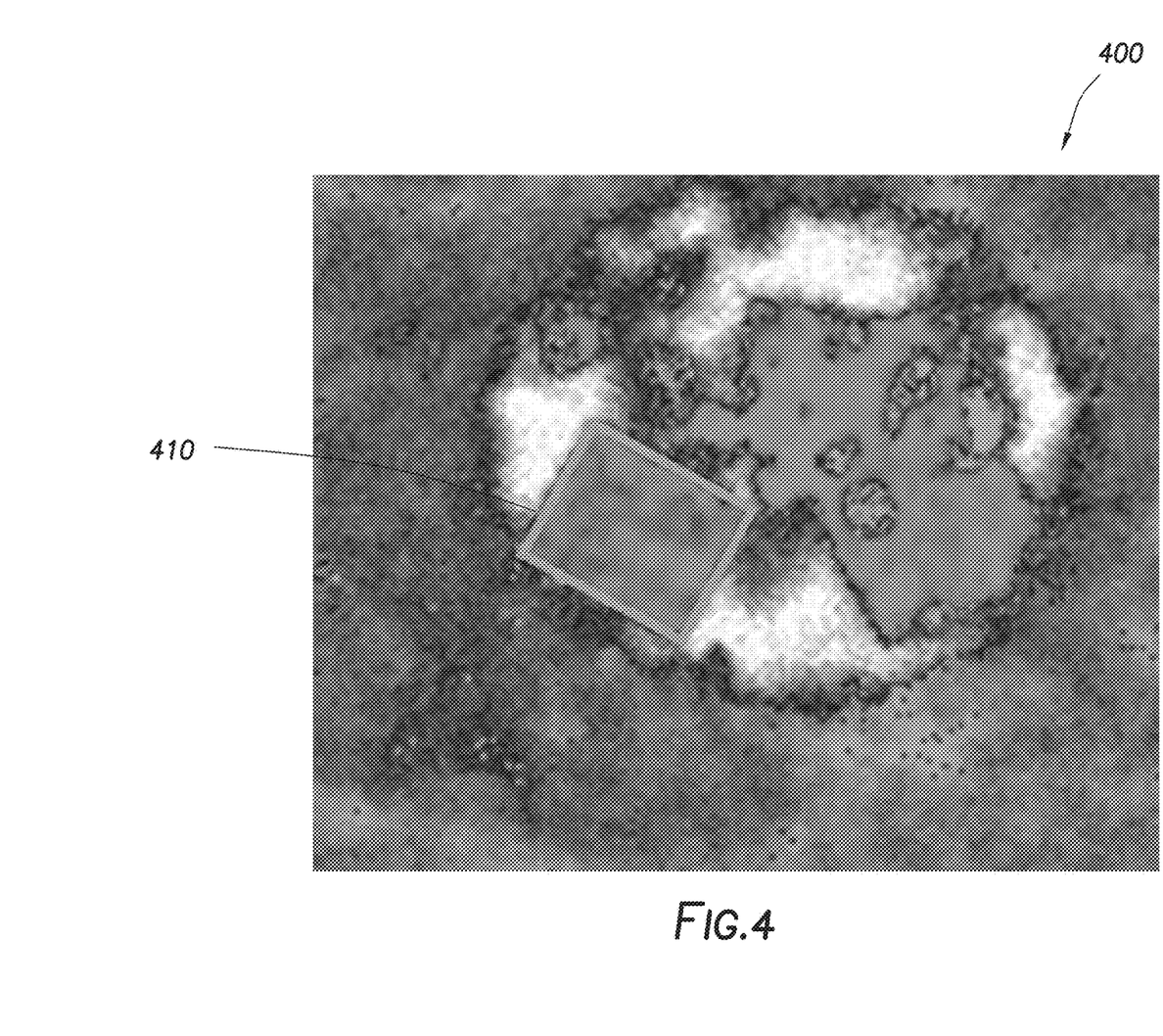
FIG. 4 is a combined optical and false color hyperspectral image as described in Example 2.
Figure 5:
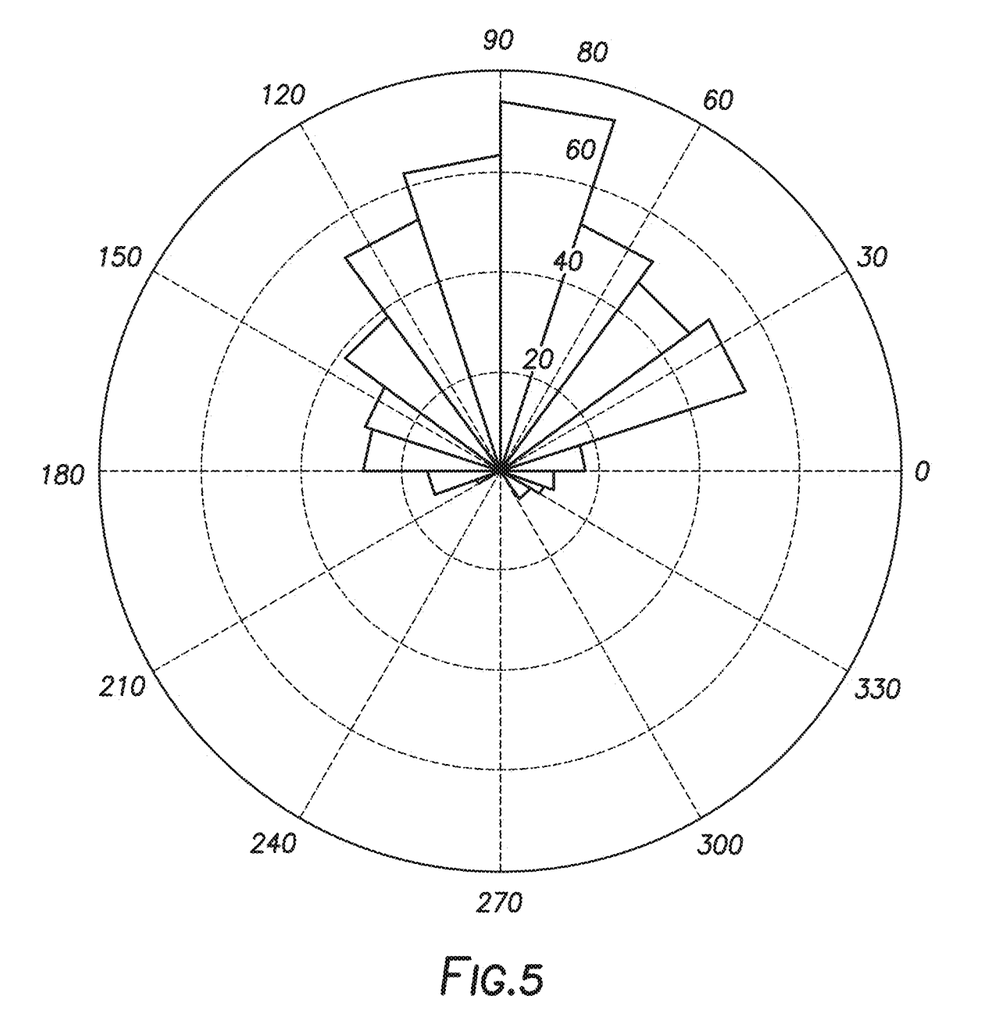
FIG. 5 is an axis orientation in polar plot as described in Example 2.

The method outlined in Example 1, may be used, for example, for a single pyrite group. In Example 2, optical image and hyperspectral colored images will be used to form the digital atlas. Single images, or overlaid images are to be used to identify pyrite. Using image processing software, or programming (such as MATLAB) to segment the image, shapes are to be fit to features and statistics reported. Combined optical and false color hyperspectral image 300 is shown in FIG. 3. Using a RGB filter or threshold, combined optical and false color hyperspectral image 300 will be converted to a 2 channel image, thereby leaving only yellow pyrite. Using MATLAB software or by hand, a rectangle will be fitted to a pyrite grain as depicted in FIG. 4. FIG. 4 depicts combined optical and false color hyperspectral image 400 with fitted rectangle 410. The length and width of the rectangle may then be measured, as well as the centroid pixel location determined. The degree to which the rectangle shape fits the grain will be determined. The orientation of long axis (degrees off of 0° in standard coordinate system)

will then be identified. The distribution of axis orientation in a polar plot may be reported as shown in FIG. 5. The statistical distribution of all pyrite across the image will be found and the statistical distribution reported. The analysis described herein with respect to pyrite will then be repeated for quartz, carbon, and fossils.

Depending on the context, all references herein to the "disclosure" may in some cases refer to certain specific embodiments only. In other cases it may refer to subject matter recited in one or more, but not necessarily all, of the claims. While the foregoing is directed to embodiments, versions and examples of the present disclosure, which are included to enable a person of ordinary skill in the art to make and use the disclosures when the information in this patent is combined with available information and technology, the disclosures are not limited to only these particular embodiments, versions and examples. Other and further embodiments, versions and examples of the disclosure may be devised without departing from the basic scope thereof and the scope thereof is determined by the claims that follow.

The invention claimed is:

1. A method comprising:
    imaging a sample surface by moving formation sample through a field of view of a microscope objective, moving the field of view over the formation sample, or moving a formation sample measurement instrument over the formation sample using a digital sample methodology, wherein the digital sample methodology uses overlapping images, representative images, selected images, or randomly determined images;
    generating a digital atlas substrate;
    mapping an area of interest by examination using a hyperspectral mapping microscopy, wherein the hyperspectral mapping microscopy is performed using a sample-scanning spectroscopy using a light spectra and wherein the sample-scanning spectroscopy is LIBS, IR, Raman, SEM-EDS, a fluorescence, a time-resolved spectroscopy or a combination thereof; and
    layering information on a digital atlas substrate.

2. The method of claim 1, wherein the imaging the sample surface is performed with a high-resolution digital optical microscopy.

3. The method of claim 2, wherein the imaging the sample surface further comprises:
    mounting the formation sample to a mounting substrate; and
    performing the imaging the formation sample using wide-field illumination techniques.

4. The method of claim 3, wherein the wide-field illumination techniques are selected from a group consisting of a reflective illumination, a transmissive illumination, a polarized light, a fluorescence, a dark-field, or a combination thereof.

5. The method of claim 1, further comprising after the layering information on the digital atlas substrate:
    comparing the light spectra to a library of one or more of minerals, clays and organic phases to identify at least one of rock constituents, abundance of rock constituents, and distribution of rock constituents.

6. The method of claim 5 further comprising the determining formation characteristics, the formation characteristics comprising one or more of a quartz-to-clay ratio, a total organic content or a thermal maturity index.

7. The method of claim 1 further comprising performing a rock texture image analysis.

8. The method of claim 7, wherein the performing the rock texture image analysis comprises use of a color-based segmentation, a shape identification, Hough Transforms, a color inversion, a boundary tracing, a Red/Green/Blue color map filtering, distribution statistics, a noise removal and an image morphology, morphological operations, or combinations thereof.

9. The method of claim 1, wherein a focused laser spot is optically translated across the sample surface.

* * * * *